United States Patent [19]

Regel

[11] Patent Number: 4,480,114

[45] Date of Patent: Oct. 30, 1984

[54] 2-(4-BIPHENYLYL)-2-(HALOPHENYL)-OXIRANE COMPOUNDS

[75] Inventor: Erik Regel, Wuppertal, Fed. Rep. of Germany

[73] Assignee: Bayer Aktiengesellschaft, Leverkusen, Fed. Rep. of Germany

[21] Appl. No.: 355,086

[22] Filed: Mar. 5, 1982

Related U.S. Application Data

[60] Continuation of Ser. No. 179,623, Aug. 20, 1980, abandoned, which is a division of Ser. No. 128,213, Mar. 7, 1980, abandoned.

[30] Foreign Application Priority Data

Mar. 28, 1979 [DE] Fed. Rep. of Germany ....... 2912288

[51] Int. Cl.$^3$ .......................................... C07D 303/08
[52] U.S. Cl. .................................. 549/563; 549/512; 549/554
[58] Field of Search ........................ 549/512, 554, 563

[56] References Cited

U.S. PATENT DOCUMENTS

| | | | |
|---|---|---|---|
| 3,335,186 | 8/1967 | Speranza | 260/348.11 |
| 3,558,639 | 1/1971 | Kirchner | 260/348.11 |
| 3,859,256 | 1/1975 | Teufel et al. | 260/348.11 |
| 4,028,415 | 6/1977 | Clark | 260/348.11 |

OTHER PUBLICATIONS

M. Delaville, Compt. Rend., vol. 184 (1927), pp. 462–463.
M. Delaville, Chemical Abstracts (1927), vol. 21, p. 2119.
A. Weissberger, Heterocyclic Compounds with Three- and Four-Membered Rings, Part One (1964), p. 234.
P. Weill, Societe Chimique de France, Bulletin, vol. 49(4) (1931), pp. 1811–1823.

Primary Examiner—Norma S. Milestone
Attorney, Agent, or Firm—Sprung Horn Kramer & Woods

[57] ABSTRACT

The invention relates to a process for the production of certain hydroxyethylazoles having antimycotic activity which comprises reacting selected phenyl-substituted oxiranes with azoles, preferably imidazoles or triazoles in the presence of an alkali metal alcoholate and a diluent. Also included in the invention are selected phenyl-substituted oxiranes as novel compounds.

3 Claims, No Drawings

2-(4-BIPHENYLYL)-2-(HALOPHENYL)-OXIRANE COMPOUNDS

This application is a continuation of application Ser. No. 179,623, filed Aug. 20, 1980, which in turn is a division of application Ser. No. 128,213, filed Mar. 7, 1980, both now abandoned.

The present invention relates to an unobvious process for the production of certain hydroxyethyl-azoles, some of which are known and which have antimycotic properties.

It has already been disclosed that certain hydroxyethyl-imidazoles are obtained when corresponding hydroxyethyl halides are reacted with imidazole, if appropriate in the presence of an acid-binding agent, such as, preferably, an excess of imidazole, or are reacted with imidazole in the form of one of their alkali metal salts, such as are obtained, for example, by treatment with sodium methylate in a suitable solvent, if appropriate in the presence of an inert organic solvent, such as, for example, dimethylformamide, at temperatures between 30° and 120° C. according to the following equation (compare DE-OS (German Published Specification) No. 2,623,129):

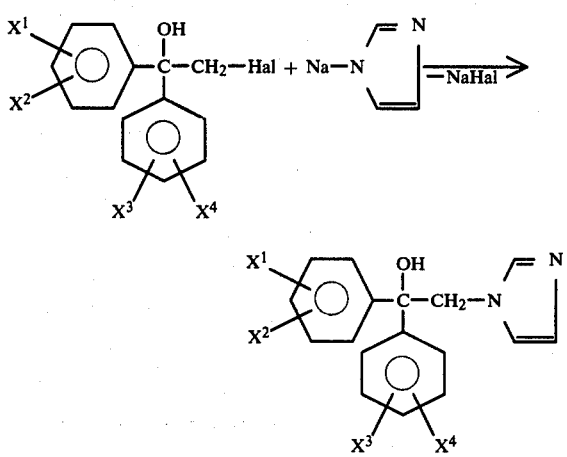

$X^1$ to $X^4$ denote hydrogen, halogen, alkyl or alkoxy and

Hal denotes halogen (chlorine or bromine)

This process has the disadvantage that it does not proceed with satisfactory yields.

According to the present invention there is provided a process for the production of a hydroxyethyl-azole of the general formula

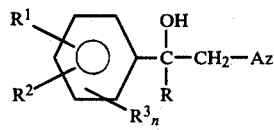

in which

Az denotes an imidazole or triazole radical,

R denotes an optionally substituted phenyl, naphthyl or tetrahydronaphthyl radical, $R^1$ denotes a hydrogen or halogen atom or an alkyl, alkoxy, halogenoalkyl, optionally substituted phenyl or cycloalkyl radical and $R^2$ denotes a hydrogen atom, or $R^1$ and $R^2$ together, in the o-position relative to each other, denote an optionally substituted, multi-membered methylene bridge or together with the phenyl ring, denote naphthyl or optionally substituted fluorenyl, $R^3$ denotes a halogen atom or an alkyl, alkoxy or halogenoalkyl radical and n is 0, 1, 2 or 3, in which an oxirane of the general formula

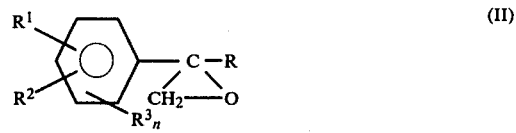

in which R, $R^1$, $R^2$, $R^3$ and n have the meanings indicated above, is reacted with an azole of the general formula $$H-Az \qquad (III)$$

in which Az has the meaning indicated above, in the presence of an alkali metal alcoholate and in the presence of a diluent.

It is to be described as exceptionally surprising that the end products are obtained in the desired high yield by the process according to the invention, and hence this process proves to be more advantageous than the process known from the state of the art.

Preferred hydroxyethyl-azoles of general formula (I) which can be prepared by the process of the present invention are those in which Az denotes an imidazol-1-yl, 1,2,4-triazol-1-yl or 1,3,4-triazol-1-yl radical;

R denotes an optionally substituted phenyl, naphthyl or tetrahydronaphthyl radical, preferred substituents being: halogen, preferably fluorine, chlorine and bromine, straight-chain or branched alkyl and alkoxy with in each case 1 to 4 carbon atoms and halogenoalkyl with 1 to 4 carbon atoms and up to 5 halogen atoms, preferably with 1 or 2 carbon atoms and up to 3 identical or different halogen atoms, halogens being, preferablt fluorine or chlorine, and trifluoromethyl being mentioned as an example;

$R^1$ denotes a hydrogen or halogen atom, in particular fluorine, chlorine or bromine, a straight-chain or branched alkyl or alkoxy radical with in each case 1 to 4 carbon atoms or a halogenoalkyl radical with 1 to 4 carbon atoms and up to 5 halogen atoms, preferably with 1 or 2 carbon atoms and up to 3 identical or different halogen atoms, halogens being, preferably, fluorine and chlorine, and trifluoromethyl being mentioned as an example; or $R^1$ denotes an optionally substituted phenyl or cycloalkyl with 3 to 7 (preferably 5 to 6) carbon atoms, preferred substituents being: halogen, preferably fluorine, chlorine or bromine, alkyl and alkoxy with 1 to 4, preferably with 1 to 2, carbon atoms and nitro.

$R^2$ denotes a hydrogen atom, or $R^1$ and $R^2$ together, in the ortho-position relative to each other, denote an optionally monosubstituted, disubstituted or polysubstituted methylene bridge with 3 to 5 methylene groups, preferred substitutents being: halogen, preferably fluorine, chlorine or bromine, and alkyl with 1 to 4, preferably with 1 to 2 carbon atoms; or $R^1$ and $R^2$, together with the phenyl ring to which they are bonded, denote naphthyl or fluorenyl, which is optionally substituted by halogen or alkyl with 1 to 2 carbon atoms;

$R^3$ denotes a halogen atom, preferably fluorine, chlorine or bromine, a straight-chain or branched alkyl or alkoxy radical with in each case 1 to 4 carbon atoms or a halogenoalkyl radical with 1 to 4 carbon atoms and up to 5 halogen atoms, preferably with 1 or 2 carbon atoms and up to 3 identical or different halogen atoms, halogens being, fluorine and chlorine, and trifluoromethyl being mentioned as an example; and n is 0, 1 or 2.

The invention includes the compounds both in the form of racemic mixtures and their optically active isomers. Racemate mixtures can be separated into the pure racemates in a known manner on the basis of the physicochemical differences of the constituents, for example by chromatography and/or fractional crystallization.

Pure racemates can be resolved according to known methods, for example by recrystallization from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

Very particularly preferred compounds of the formula (I) which can be prepared by the process of the present invention are those in which Az denotes an imidazol-1-yl or 1,2,4-triazol-1-yl radical; R denotes a phenyl radical, which is optionally monosubstituted or disubstituted by chlorine, fluorine or methyl, or denotes a naphthyl or tetrahydronaphthyl radical; $R^1$ denotes a hydrogen, fluorine, chlorine or bromine atom or a methyl, ethyl, methoxy, ethoxy or trifluoromethyl radical, or a phenyl, cyclopentyl or cyclohexy radical, which is optionally monosubstituted or disubstituted by chlorine, bromine, fluorine, nitro, methyl or methoxy; and $R^2$ denotes a hydrogen atom; or $R^1$ and $R^2$ together, in the ortho-position relative to each other, denote a tri-, tetra- or penta-methylene bridge which is optionally substituted by chlorine or methyl, or, together with the phenyl ring to which they are bonded, denote naphthyl, or fluorenyl which is optionally substituted by chlorine or methyl; $R^3$ denotes a chlorine or fluorine atom or a methyl radical; and n is 0 or 1.

If, for example, 2-(4-biphenylyl)-2-(2-chlorophenyl)-oxirane, imidazole and sodium methylate are used as starting substances, the course of the reaction can be represented by the following equation:

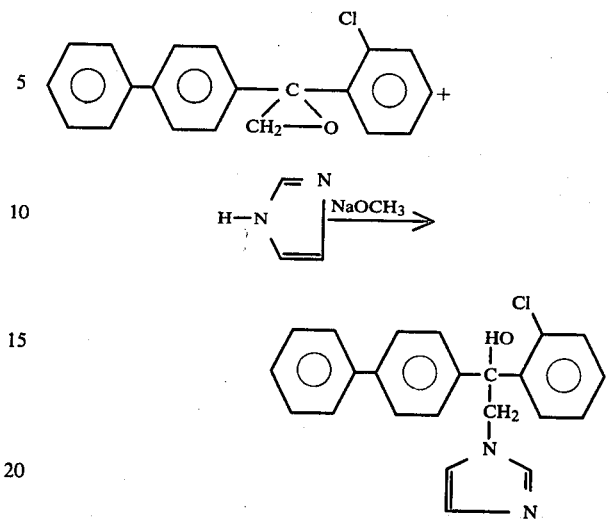

R, $R^1$, $R^2$, $R^3$ and n in the oxirane of formula (II) to be used as starting substances in carrying out the process according to the invention preferably represent those radicals which have already been mentioned as preferred for these substituents in compounds of the formula (I).

Some of the oxiranes of the formula (II) are known (compare, inter alia, U.S. Pat. Nos. 4,028,415 and 4,056,630).

The oxiranes of the general formula

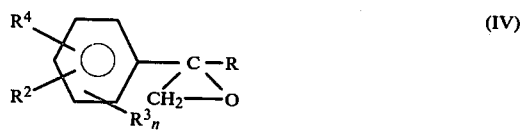

in which

R denotes an optionally substituted phenyl, naphthyl or tetrahydronaphthyl radical, $R^4$ denotes an optionally substituted phenyl or cycloalkyl radical and $R^2$ denotes hydrogen or $R^2$ and $R^4$ together, in the o-position relative to each other, denote an optionally substituted, multi-membered methylene bridge, or, together with the phenyl ring, denote naphthyl or optionally substituted fluorenyl, $R^3$ denotes a halogen atom or an alkyl, alkoxy or halogenoalkyl radical, and n is 0, 1, 2 or 3, are novel. The optional substituents and the "multi-membered methylene bridge" mean the same groups as in the legend of the formula (I) of the end products.

The oxiranes of the formula (II) are obtained by a process in which corresponding ketones of the general formula

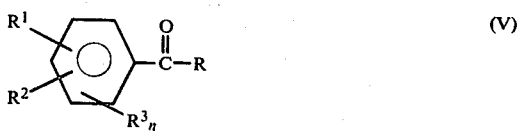

in which

R, $R^1$, $R^2$, $R^3$ and n have the meaning indicated above, (α) are reacted with dimethyloxosulphonium methylide of the formula $$(CH_3)_2SO^{\oplus}CH^{\ominus}_2 \qquad (VI)$$

in the presence of a diluent, such as dimethylsulphoxide, at temperatures between 20° and 80° C. (in this context, compare also the statements in JACS 87, 1,353–1,364 (1965)), or (β) are reacted with trimethylsulphonium methyl-sulphate of the formula $$(CH_3)_3S^{\oplus}CH_3SO_4^{\ominus} \qquad (VII)$$

in the presence of a two-phase system and if appropriate in the presence of a phase transfer catalyst, at temperatures between 0° and 100° C. (compare also the statements in Heterocycles 8, 397 (1977)).

The ketones of the formula (V) are generally known compounds of organic chemistry.

Dimethyloxosulphonium methylide of the formula (VI) is also known and is prepared in situ by reacting trimethyloxosulphonium iodide with sodium hydride (compare also the abovementioned literature reference) or sodium amide. Trimethylsulphonium methyl-sulphate is also known and is prepared in situ by reacting dimethyl sulphide with dimethyl sulphate (compare also the abovementioned literature reference).

Examples of oxiranes of the formula (II) which may be mentioned are:

(II)

| R | $R^1$ | $R^2$ | $R^3_n$ |
|---|---|---|---|
| ⌬ (phenyl) | H | H | — |
| 4-Cl-phenyl | 4-Cl | H | — |
| 3-Cl-phenyl | 3-Cl | H | — |
| 4-Cl-phenyl | 4-Cl | H | 2-Cl |
| 2-Cl-phenyl | 4-Cl | H | 2-Cl |

-continued

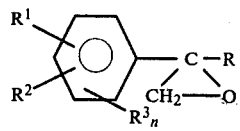
(II)

| R | $R^1$ | $R^2$ | $R^3_n$ |
|---|---|---|---|
| 4-Cl-phenyl | 4-Cl | H | 2-Cl |
| 2-Cl-phenyl | 2-Cl | H | 6-Cl |
| 4-F-phenyl | 2-Cl | H | 4-Cl |
| 4-Cl-phenyl | H | H | — |
| 4-Br-phenyl | H | H | — |
| phenyl | 2-Cl | H | 4-Cl |
| phenyl | 2-Br | H | 4-Cl |
| 2-Cl-phenyl | H | H | — |
| 2-Cl-phenyl | 2-Cl | H | 4-Cl |
| 2-Cl-phenyl | 2-Br | H | 4-Cl |
| 2-Cl-phenyl | 2-CH₃ | H | 4-Cl |

-continued $$\text{(II)}$$

Structure: R¹, R² substituted phenyl with -CH(CR)(CH₂)-O- epoxide ring, R³ₙ on ring

| R | R¹ | R² | R³ₙ |
|---|---|---|---|
| 4-Cl-phenyl | 4-Br | H | — |
| 4-Cl-phenyl | 2-Br | H | 4-Cl |
| 2,4-diCl-phenyl | 2-Br | H | 4-Cl |
| 2,4-diCl-phenyl | 4-OCH₃ | H | — |
| 2,3-diCl-phenyl | 4-OCH₃ | H | — |
| 2,3-diCl-phenyl | 4-Cl | H | 2-Br |
| phenyl | 2-Cl | H | 6-Cl |
| 2-Br-4-Cl-phenyl | 2-Cl | H | 6-Cl |
| 3,4-diCl-phenyl | 4-CH₃ | H | — |
| 3,4-diCl-phenyl | 4-Cl | H | 2-CH₃ |
| 4-Cl-phenyl | H | H | 4-OCH₃ |
| 2,6-diCl-phenyl | 4-F | H | — |
| 4-Cl-phenyl | 4-Cl | H | 2-CH₃ |
| 2-F-phenyl | 2-Cl | H | — |
| 2-F-phenyl | 4-Cl | H | — |
| 4-F-phenyl | 4-phenyl | H | — |
| 4-Cl-phenyl | 2-Cl-phenyl (4-) | H | — |
| 3-Cl-phenyl | 4-phenyl | H | — |
| 2-Cl-phenyl | 2-Cl-phenyl (4-) | H | — |
| 2-Cl-phenyl | 2,4-diCl-phenyl | H | — |
| phenyl-Cl | 2,4-diCl-phenyl | H | — |

-continued
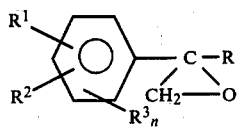
| R | R¹ | R² | R³ₙ |
|---|----|----|-----|
| 4-F-C₆H₄ | 4-Cl-C₆H₄ | H | — |
| 4-F-C₆H₄ | 2,4-Cl₂-C₆H₃ | H | — |
| 4-Cl-C₆H₄ | 4-C₆H₅ | H | — |
| 4-Cl-C₆H₄ | 4-Cl-C₆H₄ | H | — |
| 4-F-C₆H₄ | 4-Cl-C₆H₄ | H | — |
| 2-Cl-C₆H₄ | 4-Cl-C₆H₄ | H | — |
| C₆H₅ | 4-C₆H₅ | H | — |
| 2,4-Cl₂-C₆H₃ | 4-H-C₆H₄ | H | — |
| 4-Cl-C₆H₄ | 3,4-(CH₂)₃ | — | — |
| 4-Cl-C₆H₄ | 3,4-(CH₂)₄ | — | — |
| 4-Cl-C₆H₄ | 3,4-ethyl | — | — |
-continued
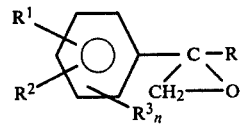
| R | R¹ | R² | R³ₙ |
|---|----|----|-----|
| 4-Cl-C₆H₄ | 3,4-Cl,ethyl-C₆H₃ | — | — |
| 2-Cl-C₆H₄ | 4-C₆H₅ | H | — |
| 2-Cl-C₆H₄ | 4-Cl-C₆H₄ | H | — |
| 2-Cl-C₆H₄ | 4-CH₃-C₆H₄ | H | — |
| 2-Cl-C₆H₄ | 4-NO₂-C₆H₄ | H | — |
| 2-Cl-C₆H₄ | 4-OCH₃-C₆H₄ | H | — |
| 2-Cl-C₆H₄ | 4-C₆H₅ | H | — |
| 2-F-C₆H₄ | 4-Cl-C₆H₄ | H | — |
| 2-F-C₆H₄ | 4-F-C₆H₄ | H | — |
| 2-F-C₆H₄ | 4-CH₃-C₆H₄ | H | — |

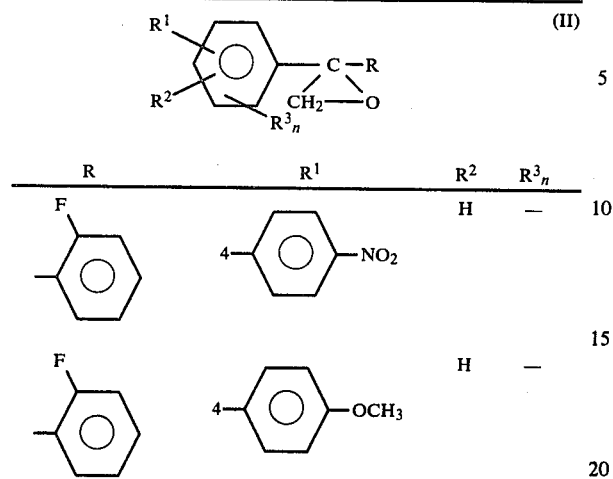

The reaction according to the invention is carried out in the presence of an alkal metal alcoholate Alkali metal alcoholates include, preferably, the methylates and ethylates of sodium and potassium.

Preferred possible diluents for the reaction according to the invention are inert organic solvents. These include, preferably, nitriles, such as, in particulare, acetonitrile; aromatic hydrocarbons, or halogenated hydrocarbons, such as benzene, toluene and dichlorobenzene; formamides, such as, in particular, dimethylformamide; or diethylformamide; halogenated diphatic hydrocarbons, such as methylene chloride or carbon tetrachloride; and hexamethylphosphoric acid triamide.

The reaction temperatures can be varied within a substantial range in carrying out the process according to the invention. Preferably, the reaction is carried out between 30° and 150° C., more preferably between 30° C. and 100° C.

In carrying out the process according to the invention, 1 to 3 mols of azole of the formula (III) and 1 to 2 mols of alkali metal alcoholate are preferably employed per mol of oxirane of the formula (II). The end products are isolated in the customary manner.

In a preferred embodiment, the oxiranes of the formula (II) obtained according to process (α) or (β) are further reacted directly, without isolation (compare the preparation examples).

The active compounds of the formula (I) which can be prepared according to the invention are distinguished by a good antimycotic activity (compare DE-OS (German Published Specification) No. 2,623,129 and German Patent Application Nos. P 28 51 143 and P 28 51 116 corresponding to U.S. application Ser. Nos. 092,804 and 092,806, each filed Nov. 9, 1979.

The process according to the invention will be illustrated with the aid of the following Examples.

EXAMPLE 1

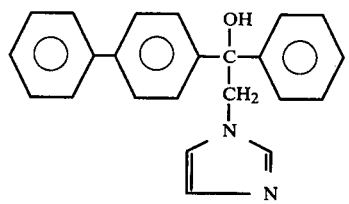

(a) Process according to the invention, without isolation of the intermediate product 120 ml of dimethylsulphoxide are added to 3.6 g (0.12 mol) of 80% strength sodium hydride and 26.4 g (0.12 mol) of trimethyloxosulphonium iodide in the course of 20 minutes. When the evolution of hydrogen has ended, a solution of 25.8 g (0.1 mol) of 4-biphenylyl phenyl ketone in 150 ml of dimethylsulphoxide is added dropwise and the mixture is subsequently stirred at 60° C. for 2 hours. 300 ml of water are added dropwise to the reaction mixture obtained. The resulting oil is separated off from the aqueous phase and dissolved in chloroform and the solution is washed with water, dried over sodium sulphate and concentrated by distilling off the solvent in vacuo. The crude 2-(4-biphenylyl)-2-phenyl-oxirane thus obtained is dissolved in 150 ml of dimethylformamide. This solution is added dropwise to a mixture of 7 g (0.13 mol) of sodium methylate, 40 ml of methanol and 15 g (0.22 mol) of imidazole. The reaction mixture is heated to 80° C. for 4 hours. Thereafter, it is concentrated in vacuo, the residue is poured onto water and the crystals which form are filtered off and washed with acetonitrile. 26.7 g (83.5% of theory) of 1-(4-biphenylyl)-2-(imidazol-1-yl)-1-phenyl-ethanol of melting point 224° C. are obtained.

(b) Comparative known process 2.45 g (0.045 mol) of sodium methylate are dissolved in 20 ml of methanol, and 5.25 g (0.077 mol) of imidazole are added. A solution of 11.1 g (0.077 mol) of 1-(4-biphenylyl)-2-chloro-1-phenyl-ethanol in 50 ml of dimethylformamide is added dropwise to this mixture and the reaction mixture is heated under reflux for 16 hours. Thereafter, it is poured onto water and the crystals which form are extracted with hot acetonitrile. 3.2 g (21% of theory) of 1-(4-biphenylyl)-2-(imidazol-1-yl)-1-phenyl-ethanol of melting point 224° C. are obtained.

(c) Preparation of the starting material

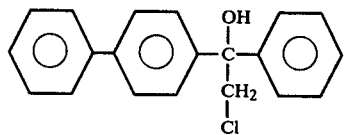

23 g (0.1 mol) of 4-phenyl-phenacyl chloride are added in portions to a solution of phenyl-magnesium bromide, obtained from 4.86 g (0.2 mol) of magnesium and 21 g (0.2 mol) of bromobenzene in 120 ml of ether. After stirring the reaction mixture for one hour, it is poured onto aqueous ammonium chloride solution. The ether phase is separated off, washed with water, dried over sodium sulphate and concentrated. 11.1 g (36% of theory) of 1-(4-biphenylyl)-2-chloro-1-phenyl-ethanol of melting point 94° C. are obtained.

EXAMPLE 2

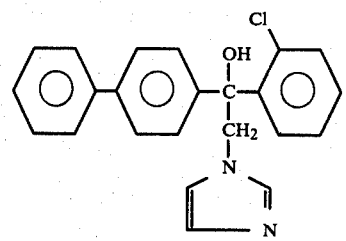

(a) Process according to the invention, with isolation of the intermediate product 3.5 g (0.065 mol) of sodium methylate are dissolved in 20 ml of methanol, and 7.5 g (0.11 mole) of imidazole are added. A solution of 15 g (0.05 mol) of 2-(4-biphenylyl)-2-(2-chlorophenyl)-oxirane in 75 ml of dimethylformamide is added dropwise to this mixture and the reaction mixture is heated to 80° C. for 1.5 hours. Thereafter, it is poured onto water and the crystals which form are filtered off and dried. 14.7 g (79% of theory) of 1-(4-biphenylyl)-1-(2-chlorophenyl)-2-imidazol-1-yl-ethanol of melting point 222° C. are obtained.

(b) Preparation of the starting material (New intermediate product of the formula (IV))

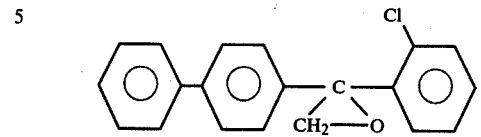

90 ml of dimethylsulphoxides are added to 2.7 g (0.09 mol) of 80% strength sodium hydride and 19.8 g (0.09 mol) of trimethyloxosulphonium iodide in the course of 20 minutes. When the evolution of hydrogen has ended, a solution of 22 g (0.075 mol) of 2-chloro-4'-phenyl-benzophenone in 60 ml of dimethylsulphoxide is added dropwise and the mixture is subsequently stirred at 50° C. for 1 hour. 200 ml of water are added to the cooled reaction mixture and the mixture is extracted by shaking with ether. The ether solution is washed with water, dried over sodium sulphate and concentrated by distilling off the solvent in vacuo. The residue is recrystallised from diisopropyl ether. 15 g (65% of theory) of 2-(4-biphenylyl)-2-(2-chlorophenyl)-oxirane of melting point 70° C. are obtained.

The compounds of the formula (I) listed in the following Table 1 can be obtained in a corresponding manner:

TABLE 1

| Ex. No. | R | $R^1$ | $R^2$ | $R^3{}_n$ | Az | Melting point (°C.) |
|---|---|---|---|---|---|---|
| 3 | 4-F-phenyl | 4-phenyl | H | — | imidazol-1-yl | 220 |
| 4 | 4-Cl-phenyl | 4-(2-Cl-phenyl) | H | — | 1H-1,2,4-triazol-1-yl | 190 |
| 5 | 2-Cl-phenyl | 4-phenyl | H | — | imidazol-1-yl | 202 |
| 6 | 4-Cl-phenyl | 4-(2-Cl-phenyl) | H | — | imidazol-1-yl | 187 |
| 7 | 2-Cl-phenyl | 4-(2-Cl-phenyl) | H | — | imidazol-1-yl | 206 |

TABLE 1-continued $$\underset{R^2}{\overset{R^1}{\diagdown}}\underset{R^3{}_n}{\bigcirc}\overset{OH}{\underset{R}{\overset{|}{C}}}-CH_2-Az \qquad (I)$$

| Ex. No. | R | R¹ | R² | R³ₙ | Az | Melting point (°C.) |
|---|---|---|---|---|---|---|
| 8 | 2-Cl-C₆H₄ | 2,4-Cl₂-C₆H₃ (4-) | H | — | imidazol-1-yl | 220 |
| 9 | 4-Cl-C₆H₄ | 2,4-Cl₂-C₆H₃ (4-) | H | — | imidazol-1-yl | 176 |
| 10 | 4-F-C₆H₄ | 2-Cl-C₆H₄ (4-) | H | — | imidazol-1-yl | 100 |
| 11 | 4-F-C₆H₄ | 2,4-Cl₂-C₆H₃ (4-) | H | — | imidazol-1-yl | 225 |
| 12 | 4-Cl-C₆H₄ | C₆H₅ (4-) | H | — | imidazol-1-yl | 230 |
| 13 | 4-Cl-C₆H₄ | 4-Cl-C₆H₄ (4-) | H | — | imidazol-1-yl | 188 |
| 14 | 4-F-C₆H₄ | 4-Cl-C₆H₄ (4-) | H | — | imidazol-1-yl | 218 |
| 15 | 2-Cl-C₆H₄ | 4-Cl-C₆H₄ (4-) | H | — | imidazol-1-yl | 206 |
| 16 | 4-Cl-C₆H₄ | 4-Cl-C₆H₄ (4-) | H | — | 1,2,4-triazol-1-yl | 189 |
| 17 | 4-F-C₆H₄ | 4-Cl-C₆H₄ (4-) | H | — | 1,2,4-triazol-1-yl | 217 |

TABLE 1-continued (I)

$$\underset{R^2}{\overset{R^1}{\text{C}_6H_3}}\!-\!\underset{R^3{}_n}{\overset{OH}{\underset{R}{C}}}\!-\!CH_2\!-\!Az$$

| Ex. No. | R | R¹ | R² | R³ₙ | Az | Melting point (°C.) |
|---|---|---|---|---|---|---|
| 18 | 2-Cl-C₆H₄ | 4-Cl-C₆H₄ | H | — | 1,2,4-triazol-1-yl | 144 |
| 19 | 2-F-C₆H₄ | 4-C₆H₅ | H | — | imidazol-1-yl | 202 |
| 20 | 2-F-C₆H₄ | 4-CH₃-C₆H₄ | H | — | imidazol-1-yl | 200 |
| 21 | 2-F-C₆H₄ | 4-C₆H₅ | H | — | imidazol-1-yl | 164 |
| 22 | 2-F-C₆H₄ | 4-C₆H₅ | H | — | 1,2,4-triazol-1-yl | 170 |
| 23 | 2-Cl-C₆H₄ | 4-Cl-C₆H₄ | H | — | imidazol-1-yl | 206 |
| 24 | 2-F-C₆H₄ | 4-Cl-C₆H₄ | H | — | imidazol-1-yl | 227 |
| 25 | 2-Cl-C₆H₄ | 4-CH₃-C₆H₄ | H | — | imidazol-1-yl | 207 |
| 26 | 2-Cl-C₆H₄ | 4-OCH₃-C₆H₄ | H | — | imidazol-1-yl | |
| 27 | 4-Cl-C₆H₄ | 4-C(CH₃)₃-C₆H₄ | H | — | imidazol-1-yl | |

TABLE 1-continued

Structure (I): R¹, R² substituted phenyl with C(OH)(R)(CH₂—Az), R³ₙ substituent

| Ex. No. | R | R¹ | R² | R³ₙ | Az | Melting point (°C.) |
|---|---|---|---|---|---|---|
| 28 | phenyl | H | H | — | imidazol-1-yl | 208–10 |
| 29 | 4-Cl-phenyl | 3-Cl | H | — | imidazol-1-yl | 165 |
| 30 | 4-Cl-phenyl | 4-Cl | H | — | imidazol-1-yl | 200 |
| 31 | 4-Cl-phenyl | 2-Cl | H | 4-Cl | imidazol-1-yl | 217–18 (xHNO₃) |
| 32 | 2,4-diCl-phenyl | 3-Cl | H | — | imidazol-1-yl | 252 |
| 33 | 4-Cl-phenyl | 4-Cl-2-ethyl-phenyl | | — | imidazol-1-yl | 242 |
| 34 | 4-Cl-phenyl | 2-ethyl-phenyl | | — | imidazol-1-yl | 238 |
| 35 | 4-Cl-phenyl | 4-Cl-2-ethyl-phenyl | | — | 1,2,4-triazol-1-yl | 186 |

The new intermediate products of the formula (IV) listed in the following table can be obtained according to Examples 1(c) and 2(b):

Structure (II): epoxide with R¹, R² substituted phenyl, R³ₙ

| Ex. No. | R | R¹ | R² | R³ₙ | Melting point/(°C.) |
|---|---|---|---|---|---|
| (IV-2) | 2-F-phenyl | 4-phenyl | H | — | 89 |

-continued
(II)
| Ex. No. | R | R¹ | R² | R³ₙ | Melting point/(°C.) |
|---|---|---|---|---|---|
| (IV-3) | F | 4-C₆H₄-CH₃ | H | — | 109 |
| (IV-4) | Cl | 4-C₆H₄-CH₃ | H | — | Oil |
| (IV-5) | F | 4-C₆H₄-Cl | H | — | Oil |
| (IV-6) | F | 4-C₆H₄-Cl (2-Cl) | H | — | Oil |
| (IV-7) | Cl | 4-C₆H₄-NO₂ | H | — | Oil |
| (IV-8) | F | 4-C₆H₄-OCH₃ | H | — | Oil |
What is claimed is:
1. A compound of the formula
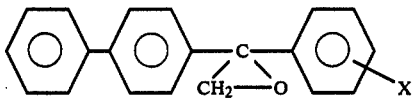
wherein X is halogen.
2. A compound of claim 1 which is 2-(4-biphenylyl)-2-(2-chlorophenyl)-oxirane.
3. A compound of claim 1 which is 2-(4-biphenylyl)-2-(4-fluorophenyl)-oxirane.
* * * * *